United States Patent
Yoshioka et al.

(10) Patent No.: US 9,804,177 B2
(45) Date of Patent: Oct. 31, 2017

(54) STIMULUS-RESPONSIVE GEL MATERIAL

(71) Applicant: Seiko Epson Corporation, Tokyo (JP)

(72) Inventors: Satomi Yoshioka, Shiojiri (JP); Hiroshi Yagi, Tatsuno (JP); Jiro Kato, Suwa (JP)

(73) Assignee: Seiko Epson Corporation (JP)

( * ) Notice: Subject to any disclaimer, the term of this patent is extended or adjusted under 35 U.S.C. 154(b) by 367 days.

(21) Appl. No.: 14/619,527

(22) Filed: Feb. 11, 2015

(65) Prior Publication Data
US 2015/0226754 A1 Aug. 13, 2015

(30) Foreign Application Priority Data
Feb. 13, 2014 (JP) .................. 2014-025180

(51) Int. Cl.
G01N 33/84 (2006.01)
G01N 31/22 (2006.01)
G01N 21/77 (2006.01)

(52) U.S. Cl.
CPC ..... G01N 33/84 (2013.01); G01N 2021/7773 (2013.01)

(58) Field of Classification Search
CPC .................. G01N 33/84; G01N 2021/7773
USPC ........................................... 435/29
See application file for complete search history.

(56) References Cited

U.S. PATENT DOCUMENTS

| | | | |
|---|---|---|---|
| 4,269,605 A | 5/1981 | Dean et al. | |
| 5,512,169 A | 4/1996 | Williams | |
| 5,898,004 A * | 4/1999 | Asher | B01J 13/00 205/777.5 |
| 6,187,599 B1 | 2/2001 | Asher et al. | |
| 8,778,508 B2 | 7/2014 | Kwong et al. | |
| 8,816,035 B2 | 8/2014 | Leclerc et al. | |
| 9,132,097 B2 | 9/2015 | Davis et al. | |
| 2002/0031841 A1 | 3/2002 | Asher et al. | |
| 2002/0106326 A1 | 8/2002 | Singaram et al. | |
| 2002/0106810 A1 | 8/2002 | Singaram et al. | |
| 2002/0197724 A1 | 12/2002 | Noronha et al. | |
| 2013/0245402 A1 * | 9/2013 | Ziaie | G01N 27/72 600/309 |
| 2014/0249203 A1 | 9/2014 | Davis et al. | |

FOREIGN PATENT DOCUMENTS

| | | |
|---|---|---|
| JP | 2001-505236 A | 4/2001 |
| JP | 3342498 B2 | 11/2002 |
| JP | 2015-140410 A | 8/2015 |
| JP | 2015-140411 A | 8/2015 |
| WO | WO-98-19787 A1 | 5/1998 |
| WO | WO-98-41859 A1 | 9/1998 |

OTHER PUBLICATIONS

ChemSpider ([3-(Methacryloylamino)phenyl]boronic acid | C10H12BNO3 | ChemSpider, retrieved from http://www.chemspider.com/Chemical-Structure.2284415.html, Apr. 4, 2017).*
Sumerlin et al. (Triply-responsive boronic acid block copolymers: solution self-assembly induced by changes in temperature, pH, or sugar concentration, Chem. Commun., 2009, 2106-2108).*
U.S. Appl. No. 14/618,221, filed Feb. 10, 2015, Satomi Yoshioka et al.
U.S. Appl. No. 14/618,291, filed Feb. 10, 2015, Satomi Yoshioka et al.
Weber et al., "Letter to the Editor: Novel Lactate and pH Biosensor for Skin and Sweat Analysis Based on Single Walled Carbon Nanotubes", Sensors and Actuators B 117 (2006) pp. 308-313.
Morris et al., "Wearable Technology for Bio-Chemical Analysis of Body Fluids During Exercise", 30th Annual International IEEE EMBS Conference, Vancouver, British Colombia, Canada (Aug. 20-24, 2008) pp. 5741-5744.

* cited by examiner

Primary Examiner — Ling Choi
Assistant Examiner — Chun-Cheng Wang
(74) Attorney, Agent, or Firm — Harness, Dickey & Pierce, P.L.C.

(57) ABSTRACT

A stimulus-responsive gel material includes: a polymeric material containing as constituent components, a first monomer having a chemical structure represented by the following formula (1) and a second monomer having higher hydrophobicity than the first monomer; fine particles having an average particle diameter of 10 nm or more and 1000 nm or less; and a solvent, wherein the wavelength of a reflected light from the material changes according to the concentration of salt to come in contact with the material.

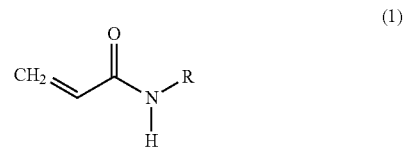

(1)

In the formula (1), R is a substituent containing at least a carbon atom and a hydrogen atom, and when the number of carbon atoms in R is denoted by n and the number of oxygen atoms in R is denoted by m, n-m is an integer of 3 or more.

7 Claims, No Drawings

STIMULUS-RESPONSIVE GEL MATERIAL

BACKGROUND

1. Technical Field

The present invention relates to a stimulus-responsive gel material.

2. Related Art

At present, as a method for obtaining in vivo biological information, a biochemical test in which the composition of the blood obtained by blood collection is generally performed. This test is mostly performed in medical institutions.

Above all, a blood glucose sensor has been widely used in diabetic patients, and also a simple lactic acid sensor is getting widely used in athletes.

However, both are test methods involving blood collection using an invasive technique.

On the other hand, as a method using a non-invasive technique, a sensor targeting a component of sweat has been studied (see, for example, Wearable Technology for Bio-Chemical Analysis of Body Fluids During Exercise 30th Annual International IEEE EMBS Conference Vancouver, British Columbia, Canada, Aug. 20-24, 2008, and Novel lactate and pH biosensor for skin and sweat analysis based on single walled carbon nanotubes/Sensors and Actuators B 117 (2006) 308-313).

However, such a method employs an electrode method using a dye or an enzyme and therefore has the following problems: a processing section and a display section for displaying data measured by an electrode are needed; a power source (a battery) for the electrode, the processing section, and the display section is needed; etc., and also has other problems that the structure is complicated and also the weight is large.

Further, the enzyme is generally expensive and is susceptible to temperature, humidity, etc., and therefore hardly exhibits stable properties, and also has a problem that the reliability of quantitative performance is low.

In addition, the enzyme greatly varies in quality among production lots or depending on manufacturers. Further, its properties change greatly over time, and therefore, it is necessary to perform calibration using a standard solution having a known concentration before use.

SUMMARY

An advantage of some aspects of the invention is to provide a stimulus-responsive gel material capable of easily and stably detecting the concentration of salt in a wide concentration range.

A stimulus-responsive gel material according to an aspect of the invention includes: a polymeric material containing as constituent components, a first monomer having a chemical structure represented by the following formula (1) and a second monomer having higher hydrophobicity than the first monomer; fine particles having an average particle diameter of 10 nm or more and 1000 nm or less; and a solvent, wherein the wavelength of a reflected light from the material changes according to the concentration of salt to come in contact with the material.

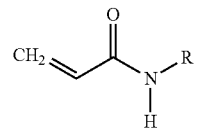

(1)

In the formula (1), R is a substituent containing at least a carbon atom and a hydrogen atom, and when the number of carbon atoms in R is denoted by n and the number of oxygen atoms in R is denoted by m, n-m is an integer of 3 or more.

According to this configuration, a stimulus-responsive gel material capable of easily and stably detecting the concentration of salt in a wide concentration range can be provided.

In the stimulus-responsive gel material according to the aspect of the invention, it is preferred that the polymeric material has a logP value of 0.62 or more and 0.81 or less.

In the stimulus-responsive gel material according to the aspect of the invention, it is preferred that the first monomer has a logP value of 0.46 or more and 0.78 or less.

In the stimulus-responsive gel material according to the aspect of the invention, it is preferred that the first monomer is N-isopropylacrylamide.

In the stimulus-responsive gel material according to the aspect of the invention, it is preferred that the second monomer has a logP value of 1.1 or more and 1.6 or less.

In the stimulus-responsive gel material according to the aspect of the invention, it is preferred that the second monomer has a phenylboronic acid structure.

In the stimulus-responsive gel material according to the aspect of the invention, it is preferred that when the content of the first monomer in the polymeric material is denoted by $X_1$ (mol %) and the content of the second monomer therein is denoted by $X_2$ (mol %), $X_1$ and $X_2$ satisfy the following relationship: $0.07 \leq X_2/X_1 \leq 0.45$.

In the stimulus-responsive gel material according to the aspect of the invention, it is preferred that water is contained as the solvent.

DESCRIPTION OF EXEMPLARY EMBODIMENTS

Hereinafter, preferred embodiments of the invention will be described in detail.

Stimulus-Responsive Gel Material

The stimulus-responsive gel material of this embodiment includes a polymeric material, fine particles, and a solvent and is deformed, for example, expanded or contracted, according to a change in the concentration of salt to come in contact with the material, and therefore is configured to enable the detection of the concentration of salt.

In this embodiment, the concentration of salt can be detected in this manner, however, because of being a gel material, as compared with the case of using an enzyme in the past, the stability is high, and also a variation in properties among lots or the like is small. Further, because of being a gel material (a gel material in which a structural color due to colloidal crystals appears) including as a constituent component, a polymeric material containing monomers (a first monomer and a second monomer), which satisfy predetermined conditions as described in detail below, as constituent components, the concentration of salt can be easily and reliably detected over a wide concentration range. Further, a user or the like can easily and reliably recognize the detected concentration of salt even if a power source is not used or the structure is not made complicated.

In addition, it is not necessary to use an expensive material such as an enzyme, and therefore, this stimulus-responsive gel material is advantageous also from the viewpoint of cost.

Polymeric Material

The polymeric material constituting the stimulus-responsive gel material contains as constituent components, a first monomer having a chemical structure represented by the following formula (1) and a second monomer having higher hydrophobicity than the first monomer.

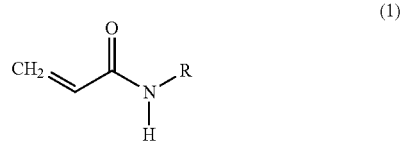

(1)

In the formula (1), R is a substituent containing at least a carbon atom and a hydrogen atom, and when the number of carbon atoms in R is denoted by n and the number of oxygen atoms in R is denoted by m, n-m is an integer of 3 or more.

First Monomer

The polymeric material constituting the stimulus-responsive gel material contains a first monomer having a chemical structure represented by the above formula (1) as a constituent component.

By including the first monomer, the stimulus-responsive gel material can be made to undergo a deformation reaction with salt.

This is considered to be due to the following reasons. That is, by including the first monomer having a chemical structure represented by the above formula (1) as a constituent component, the hydrophilic and hydrophobic properties of the polymeric material change reversibly according to the concentration of surrounding salt. More specifically, in the case where the concentration of salt is low, a solvent component efficiently forms a hydrogen bond with the —CONHR group in the formula (1) so that the monomer is put into a hydrophilic state. On the other hand, when the concentration of salt is increased, due to a salting-out effect, the solvent component capable of forming a hydrogen bond is stripped from the —CONHR group in the formula (1) so as to break the hydrogen bond with the —CONHR group in the formula (1), whereby the hydrophobicity is increased. When the hydrophobicity is increased, the molecular structure of the polymeric material containing the first monomer as a constituent component is converted into a globule structure, and thus, the stimulus-responsive gel material as a whole is deformed.

As an index indicating the degree of hydrophobicity of a monomer, a logP value is used.

This logP value refers to an n-octanol/water partition coefficient when using n-octanol and water as solvents, and it can be said that as the logP value is larger, the hydrophobicity is higher. In the embodiment of the invention, as the logP value, a value at 25° C. is adopted. Further, the logP value may be experimentally obtained or a calculated value may be used.

The logP value of the first monomer is preferably 0.46 or more and 0.78 or less, more preferably 0.46 or more and 0.61 or less, further more preferably 0.59 or more and 0.61 or less.

According to this, while making the ability to retain the solvent of the stimulus-responsive gel material particularly excellent, the sensitivity for salt can be particularly enhanced.

As the index of hydrophobicity, other than the logP value as described above, for example, a LogD value, any of various solubility parameters such as a Hansen solubility parameter (HSP), or the like can also be adopted.

When the polymeric material contains plural types of first monomers, it is preferred that all of the first monomers satisfy the above-described conditions for the logP value.

The first monomer may be any as long as it has a chemical structure represented by the above formula (1), and examples thereof include N-[3-(dimethylamino)propyl]methacrylamide, N-isopropylacrylamide, diacetoneacrylamide, N-t-butylacrylamide, and N,N-diethylacrylamide, and one type or a combination of two or more types selected therefrom can be used. However, N-isopropylacrylamide is preferred.

According to this, while making the ability to retain the solvent of the stimulus-responsive gel material further excellent, the sensitivity for salt can be further enhanced.

The content $X_1$ of the first monomer in the polymeric material is preferably 65 mol % or more and 97 mol % or less, more preferably 77 mol % or more and 95 mol % or less, further more preferably 82 mol % or more and 93 mol % or less.

According to this, while making the ability to retain the solvent of the stimulus-responsive gel material particularly excellent, the sensitivity for salt can be sufficiently enhanced.

Second Monomer

The polymeric material constituting the stimulus-responsive gel material contains a second monomer having higher hydrophobicity than the first monomer as a constituent component.

By including the second monomer having higher hydrophobicity than the first monomer as a constituent component along with the first monomer in the polymeric material in this manner, the sensitivity for salt is improved, and the concentration range in which the concentration of salt can be detected with the stimulus-responsive gel material can be increased.

This is considered to be due to the following reasons. That is, as described above, by including the first monomer as a constituent component in the polymeric material, the stimulus-responsive gel material is made to undergo a deformation reaction with salt. However, in the case where the polymeric material contains only the first monomer as a constituent component, the hydrophilicity of the polymeric material as a whole is too high, and therefore, in a state where the concentration of surrounding salt is low, the salting-out effect as described above is not sufficiently exhibited, and thus, the sensitivity for salt is low. On the other hand, by including the second monomer along with the first monomer, the "hydrophilicity of the polymeric material (the formation of a hydrogen bond between the polymeric material and the solvent)" can be moderately decreased, and thus, the detection of salt even at low concentrations can be performed. Further, not only the detection of salt at low concentrations can be performed in this manner, but also in a sufficiently high concentration range, the hydrophilic and hydrophobic properties of the polymeric material can change continuously and reversibly, and therefore, the detection and quantitative determination of the concentration of salt can be performed over a wide concentration range.

The second monomer may be any as long as it has higher hydrophobicity than the first monomer, however, the logP value of the second monomer is preferably 1.1 or more and 1.6 or less, more preferably 1.11 or more and 1.5 or less, further more preferably 1.13 or more and 1.4 or less.

According to this, while making the ability to retain the solvent of the stimulus-responsive gel material sufficiently excellent, the sensitivity for salt of the stimulus-responsive gel material is particularly enhanced, and the concentration range in which the detection and quantitative determination of the concentration of salt can be performed can be particularly increased.

When the polymeric material contains plural types of second monomers, it is preferred that all of the second monomers satisfy the above-described conditions for the logP value.

The second monomer may be any as long as it has higher hydrophobicity than the first monomer, but preferably has a phenylboronic acid structure.

According to this, while making the ability to retain the solvent of the stimulus-responsive gel material sufficiently excellent, the sensitivity for salt of the stimulus-responsive gel material is further enhanced, and the concentration range in which the detection and quantitative determination of the concentration of salt can be performed can be further increased.

Although varying depending on the combination with the first monomer, examples of a compound which can be used as the second monomer include N-isopropylmethacrylamide, N-(butoxymethyl)acrylamide, N-(isobutoxymethyl)acrylamide, 3-acrylamidephenylboronic acid, and N-phenylacrylamide, and one type or a combination of two or more types selected therefrom can be used. Above all, 3-acrylamidephenylboronic acid is preferred.

According to this, while making the ability to retain the solvent of the stimulus-responsive gel material particularly excellent, the sensitivity for salt of the stimulus-responsive gel material is further enhanced, and the concentration range in which the detection and quantitative determination of the concentration of salt can be performed can be more remarkably increased.

The content $X_2$ of the second monomer in the polymeric material is preferably 2.0 mol % or more and 30 mol % or less, more preferably 4.0 mol % or more and 20 mol % or less, further more preferably 4.5 mol % or more and 17 mol % or less.

According to this, while making the ability to retain the solvent of the stimulus-responsive gel material excellent, the sensitivity for salt of the stimulus-responsive gel material is particularly enhanced, and the concentration range in which the detection and quantitative determination of the concentration of salt can be performed can be further increased.

When the content of the first monomer in the polymeric material is denoted by $X_1$ (mol %) and the content of the second monomer therein is denoted by $X_2$ (mol %), $X_1$ and $X_2$ preferably satisfy the following relationship: $0.07 \leq X_2/X_1 \leq 0.45$, more preferably satisfy the following relationship: $0.07 \leq X_2/X_1 \leq 0.18$.

According to this, while making the ability to retain the solvent of the stimulus-responsive gel material excellent, the sensitivity for salt of the stimulus-responsive gel material is particularly enhanced, and the concentration range in which the detection and quantitative determination of the concentration of salt can be performed can be further increased.

Other Constituent Components

The polymeric material may contain, in addition to the above-described first monomer and second monomer, other constituent components.

As such components, for example, a crosslinking agent component can be used.

According to this, the polymeric material has a crosslinked structure so as to have a three-dimensional network structure. As a result, the ability to retain the solvent of the stimulus-responsive gel material can be particularly enhanced, and thus, a favorable gel state can be maintained stably over a long period of time. That is, the stimulus-responsive gel material has excellent durability.

As the crosslinking agent component, a compound having two or more polymerizable functional groups can be used, and specific examples thereof include ethylene glycol, propylene glycol, trimethylolpropane, glycerin, polyoxyethylene glycol, polyoxypropylene glycol, polyglycerin, N,N'-methylenebisacrylamide, N,N-methylene-bis-N-vinylacetamide, N,N-butylene-bis-N-vinylacetamide, tolylene diisocyanate, hexamethylene diisocyanate, allylated starch, allylated cellulose, diallyl phthalate, tetraallyloxyethane, pentaerythritol triallyl ether, trimethylolpropane triallyl ether, diethylene glycol diallyl ether, and triallyl trimellitate, and one type or a combination of two or more types selected therefrom can be used.

The content of the crosslinking agent component in the polymeric material is preferably 0.5 mol % or more and 6.0 mol % or less, more preferably 0.8 mol % or more and 5.0 mol % or less, further more preferably 1.1 mol % or more and 4.0 mol % or less.

According to this, the degree of crosslinking of the polymeric material can be made to fall within a more favorable range, and while remarkably exhibiting the effect as described above, the flexibility of the polymeric material can be made more appropriate.

The polymeric material may contain a monomer component other than the above-described first monomer and second monomer.

The logP value of the polymeric material is preferably 0.62 or more and 0.81 or less, more preferably 0.62 or more and 0.69 or less.

According to this, while making the ability to retain the solvent of the stimulus-responsive gel material particularly excellent, the sensitivity for salt of the stimulus-responsive gel material can be particularly enhanced.

In this embodiment, the logP value of the polymeric material refers to the sum of the product of logP value of each constituent component (each constituent monomer) of the polymeric material by the molar ratio thereof in the polymeric material. That is, assuming that the polymeric material contains constituent components A, B, C, . . . , and the logP values of these constituent components are denoted by $LogP_A$, $LogP_B$, $LogP_C$, . . . , and the contents (mol %) of these constituent components in the polymeric material are denoted by $C_A$, $C_B$, $C_C$, . . . , the logP value of the polymeric material is represented by $0.01 \times C_A \times LogP_A + 0.01 \times C_B \times LogP_B + 0.01 \times C_C \times LogP_C \ldots$, The content of the polymeric material in the stimulus-responsive gel material is preferably 0.7 mass % or more and 36.0 mass % or less, more preferably 2.4 mass % or more and 27.0 mass % or less.

According to this, the stimulus-responsive gel material is made particularly easy to handle, and also has particularly high sensitivity and quantitative performance for salt.

Solvent

The stimulus-responsive gel material includes a solvent.

According to this, the above-described polymeric material can be gelled.

As the solvent, a solvent capable of forming a hydrogen bond can be preferably used, and specific examples thereof include water and a variety of alcohols such as methanol and ethanol, and one type or a combination of two or more types selected therefrom can be used. However, in particular, a solvent containing water is preferred.

According to this, the detection and quantitative determination of the concentration of salt can be performed over a wider concentration range, and also the solvent is more favorably retained in the stimulus-responsive gel material, and thus, the stability and reliability of the stimulus-responsive gel material can be particularly enhanced.

The content of the solvent (the solvent capable of forming a hydrogen bond) in the stimulus-responsive gel material is preferably 30 mass % or more and 95 mass % or less, more preferably 50 mass % or more and 90 mass % or less.

According to this, the stimulus-responsive gel material is made particularly easy to handle, and also has particularly high sensitivity and quantitative performance for salt.

Fine Particles

The stimulus-responsive gel material includes fine particles having an average particle diameter of 10 nm or more and 1000 nm or less.

According to this, when the stimulus-responsive gel material receives a stimulus of a change in the concentration of salt, a change in the structural color of colloidal crystals formed by the fine particles is easily recognized, and therefore, the detection and quantitative determination of the concentration of salt can be easily and reliably performed.

By including the fine particles in the stimulus-responsive gel material, the wavelength of a reflected light largely changes according to the concentration of salt with which the stimulus-responsive gel material comes in contact, and thus, the quantitative performance for the concentration of salt can be enhanced.

In this embodiment, the average particle diameter refers to an average particle diameter on the volume basis, and can be obtained by, for example, measurement with a particle size distribution analyzer employing a Coulter counter method (model: TA-II, manufactured by Coulter Electronics, Inc.) using an aperture of 50 μm for a dispersion obtained by adding a sample to methanol and dispersing the sample therein for 3 minutes with an ultrasonic disperser.

Examples of the constituent material of the fine particles include inorganic materials such as silica and titanium oxide; and organic materials (polymers) such as polystyrene, polyester, polyimide, polyolefin, poly(methyl (meth) acrylate), polyethylene, polypropylene, polyether sulfone, nylon, polyurethane, polyvinyl chloride, and polyvinylidene chloride, however, the fine particles are preferably silica fine particles. According to this, the fine particles have particularly excellent shape stability and the like, and thus, the durability, reliability, and the like of the stimulus-responsive gel material can be particularly enhanced. Silica fine particles are relatively easily available as those having a sharp particle size distribution (monodispersed fine particles), and therefore are advantageous also from the viewpoint of stable production and supply of the stimulus-responsive gel material.

The shape of the fine particles is not particularly limited, but is preferably a spherical shape. According to this, the structural color due to colloidal crystals is more reliably visually recognized, and the quantitative determination of the concentration of salt can be more easily and more reliably performed.

The average particle diameter of the fine particles may be 10 nm or more and 1000 nm or less, but is preferably 20 nm or more and 500 nm or less.

According to this, the effect of including the fine particles in the stimulus-responsive gel material as described above is more remarkably exhibited.

The stimulus-responsive gel material may include a plurality of different types of fine particles.

The content of the fine particles in the stimulus-responsive gel material is preferably 1.6 mass % or more and 36 mass % or less, more preferably 4.0 mass % or more and 24 mass % or less.

According to this, the effect of including the fine particles in the stimulus-responsive gel material as described above is more remarkably exhibited.

Other Components

The stimulus-responsive gel material may include components other than the above-described components (other components).

Examples of such components include a colorant, a slipping agent (a leveling agent), an antifungal agent, a preservative, an antioxidant, a solvent which does not form a hydrogen bond, and a moisturizing agent.

Shape of Whole Stimulus-Responsive Gel Material

The shape of the stimulus-responsive gel material may be any, and examples thereof include a sheet, (a film), a plate, a block, a string, a tube, and a particle.

Application of Stimulus-Responsive Gel Material

The stimulus-responsive gel material is capable of easily and stably detecting the concentration of salt in a wide concentration range, and has excellent quantitative performance.

Specific application of the stimulus-responsive gel material include detection units for salt contained in substances secreted outside the body (for example, sweat, urine, saliva, etc.), detection units for salt contained in foods, detection units for salt contained in water (for example, salt contained in brackish waters, rivers, paddies, etc.), and cell culture monitors.

Hereinabove, preferred embodiments of the invention are described, however, the invention is not limited thereto.

EXAMPLES

Hereinafter, a more detailed description will be made with reference to Examples, however, the invention is not limited only to these Examples.

(1) Production of Stimulus-Responsive Gel Material

Example 1

In a container, a 15 mass % aqueous solution of N-isopropylacrylamide (1.0 mL) as the first monomer, a 5 mass % aqueous solution of 3-acrylamidephenylboronic acid (0.5 mL) as the second monomer, a 2 mass % aqueous solution of N,N'-methylenebisacrylamide (0.2 mL) as the crosslinking agent, and a 3.3 mass % aqueous solution of a compound represented by the following formula (2) (0.06 mL) as the polymerization initiator were mixed, and further, an aqueous dispersion of silica nanoparticles (average particle diameter: 80 nm) having a silica concentration of 40 mass % (0.5 mL) was added in small portions thereto, followed by stirring, whereby a mixed liquid was obtained.

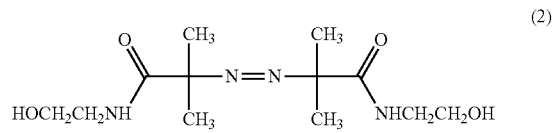

Subsequently, to the mixed liquid, an ion exchange resin (half the volume of the mixed liquid) was added, and the resulting mixture was stirred well until a structural color appeared.

Subsequently, the mixed liquid in which the structural color appeared was separated from the ion exchange resin by collecting only the mixed liquid with a micropipette and placed in another container (a container with a septum cap).

Thereafter, a degassing treatment was performed by nitrogen bubbling. The degassing time was set to 300 seconds, and the nitrogen gas flow rate was set to 10 mL/min.

On the other hand, a glass plate with a size of 18 mm×18 mm (a first glass substrate) subjected to a washing treatment, and thereafter further subjected to a silane coupling treatment was prepared. To this first glass substrate, a spacer with a thickness of 0.1 mm was attached, and further, a second glass substrate (20 mm×20 mm) which is larger than the first glass substrate was also attached thereto with the spacer interposed therebetween, whereby a cell was prepared.

Subsequently, the cell was placed in a transparent container (a glass container) with a septum cap, and the container was filled with nitrogen gas.

Subsequently, the mixed liquid in which the structural color appeared was aspirated using a syringe with a needle and injected into the cell through the septum cap with the needle.

Thereafter, the needle was pulled out from the septum cap, and the cap was further sealed with Parafilm.

Subsequently, the cell in the transparent container was irradiated with ultraviolet light (peak wavelength: 365 nm, SP-7, manufactured by Ushio, Inc.) to cause a polymerization reaction of the mixed liquid.

Thereafter, the cell was taken out from the transparent container and immersed in pure water. In water, the second glass substrate was peeled off from the first glass substrate, whereby a film-shaped stimulus-responsive gel material was obtained.

In the above description, the procedures in which the temperature was not particularly specified were performed at room temperature (25° C.).

Examples 2 to 11

Stimulus-responsive gel materials were produced in the same manner as in the above-described Example 1 except that the types and amounts of the components to be used for preparing the mixed liquid were changed.

Comparative Example 1

A stimulus-responsive gel material was produced in the same manner as in the above-described Example 1 except that in the preparation of the mixed liquid, the second monomer was not used, and the amount of the first monomer was increased by an amount equal to the amount of the second monomer.

Comparative Example 2

A stimulus-responsive gel material was produced in the same manner as in the above-described Example 1 except that in the preparation of the mixed liquid, the first monomer was not used, and the amount of the second monomer was increased by an amount equal to the amount of the first monomer.

Comparative Example 3

A stimulus-responsive gel material was produced in the same manner as in the above-described Example 1 except that in the preparation of the mixed liquid, methoxysilylpropyl acrylate was used in place of the first monomer.

Comparative Example 4

A stimulus-responsive gel material was produced in the same manner as in the above-described Example 1 except that in the preparation of the mixed liquid, N,N-diethylacrylamide was used in place of the second monomer.

The configurations and the like of the stimulus-responsive gel materials of the above respective Examples and Comparative Examples are summarized in Table 1. In Table 1, N-isopropylacrylamide (logP value: 0.598) as the first monomer is denoted by "1A", N-[3-(dimethylamino)propyl]methacrylamide (logP value: 0.463) as the first monomer is denoted by "1B", diacetoneacrylamide (logP value: 0.604) as the first monomer is denoted by "1C", N-t-butylacrylamide (logP value: 0.676) as the first monomer is denoted by "1D", N,N-diethylacrylamide (logP value: 0.773) as the first monomer is denoted by "1E", N-isopropylmethacrylamide (logP value: 1.16) as the second monomer is denoted by "2A", N-(butoxymethyl)acrylamide (logP value: 1.252) as the second monomer is denoted by "2B", N-(isobutoxymethyl)acrylamide (logP value: 1.259) as the second monomer is denoted by "2C", 3-acrylamidephenylboronic acid (logP value: 1.399) as the second monomer is denoted by "2D", N-phenylacrylamide (logP value: 1.524) as the second monomer is denoted by "2E", methoxysilylpropyl acrylate (logP value: 0.862) is denoted by "1'A", N,N-dimethylacrylamide (logP value: 0.089) is denoted by "2'A", and N,N'-methylenebisacrylamide as the crosslinking agent is denoted by "BA1". As the logP values of the constituent components of the polymeric material, values calculated using CAChe were adopted.

TABLE 1

| | Polymeric material | | | | | Fine particles | | Solvent | |
|---|---|---|---|---|---|---|---|---|---|
| | Constituent component | | LogP value of first monomer | LogP value of second monomer | LogP value of polymeric material | Content (parts by mass) | Constituent material | Content (parts by mass) | Constituent component | Content (parts by mass) |
| | Type | Blending ratio (molar ratio) | | | | | | | | |
| Example 1 | 1A/2D/BA1 | 84.9/12.6/2.5 | 0.598 | 1.399 | 0.654 | 9.7 | Silica | 11 | Water | 79.5 |
| Example 2 | 1A/2D/BA1 | 82.6/14.9/2.4 | 0.598 | 1.399 | 0.698 | 10.2 | Silica | 11 | Water | 78.5 |
| Example 3 | 1C/2B/BA1 | 82.7/14.8/2.4 | 0.604 | 1.252 | 0.686 | 10.2 | Silica | 11 | Water | 78.5 |
| Example 4 | 1A/2C/BA1 | 87.0/10.4/2.6 | 0.598 | 1.259 | 0.652 | 9.6 | Silica | 11 | Water | 79.0 |
| Example 5 | 1A/2A/BA1 | 91.0/6.7/2.2 | 0.598 | 1.16 | 0.623 | 10.8 | Silica | 11 | Water | 77.9 |
| Example 6 | 1A/2A/BA1 | 91.0/6.7/2.2 | 0.598 | 1.16 | 0.623 | 16.1 | Silica | 11 | Water | 72.5 |
| Example 7 | 1B/2A/BA1 | 67.8/30.2/2.0 | 0.463 | 1.16 | 0.664 | 9.0 | Silica | 11 | Water | 79.6 |
| Example 8 | 1B/2A/BA1 | 67.4/30.1/2.5 | 0.463 | 1.16 | 0.661 | 8.9 | Silica | 11 | Water | 79.8 |

TABLE 1-continued

| | Polymeric material | | | | | Fine particles | | Solvent | |
|---|---|---|---|---|---|---|---|---|---|
| | Constituent component | | LogP value of first monomer | LogP value of second monomer | LogP value of polymeric material | Content (parts by mass) | Constit-uent material | Content (parts by mass) | Constit-uent component | Content (parts by mass) |
| | Type | Blending ratio (molar ratio) | | | | | | | | |
| Example 9 | 1D/2D/BA1 | 87.8/9.7/2.4 | 0.676 | 1.399 | 0.730 | 9.9 | Silica | 11 | Water | 78.7 |
| Example 10 | 1E/2E/BA1 | 93.5/4.5/2.1 | 0.773 | 1.524 | 0.791 | 11.5 | Silica | 11 | Water | 77.1 |
| Example 11 | 1E/2E/BA1 | 91.4/6.6/2.0 | 0.773 | 1.524 | 0.807 | 11.0 | Silica | 11 | Water | 77.6 |
| Comparative Example 1 | 1A/BA1 | 97.6/2.4 | 0.598 | — | 0.584 | 9.9 | Silica | 11 | Water | 78.7 |
| Comparative Example 2 | 2A/BA1 | 97.3/2.7 | — | 1.16 | 1.129 | 9.9 | Silica | 11 | Water | 78.7 |
| Comparative Example 3 | 1'A/2A/BA1 | 74.8/23.0/2.3 | 0.862 | 1.16 | 0.911 | 10.5 | Silica | 11 | Water | 78.2 |
| Comparative Example 4 | 1A/2'A/BA1 | 82.0/15.6/2.4 | 0.598 | 0.089 | 0.490 | 9.6 | Silica | 11 | Water | 79.0 |

(2) Evaluation of Stimulus-Responsive Gel Material (2.1) Change in Reflection Spectrum of Gel Film with respect to Change in Concentration of Salt In each of the above respective Examples and Comparative Examples, a film-shaped stimulus-responsive gel material (16 mm×16 mm) produced on the first glass substrate was immersed in pure water in a container.

Subsequently, after excess water of the stimulus-responsive gel material taken out from pure water was removed, the stimulus-responsive gel material was placed in a plastic container with a diameter of 6 cm filled with an aqueous salt solution for evaluation having a predetermined concentration, and immersed in the aqueous salt solution.

The stimulus-responsive gel material was left to stand in the aqueous salt solution for 5 minutes, and it was confirmed that the color of the stimulus-responsive gel material no longer changed and was stabilized.

Thereafter, with respect to the stimulus-responsive gel material whose color was stabilized, color measurement was performed on the side of the first glass substrate using SpectroEye manufactured by X-Rite Incorporated, and the data of the reflection spectrum of the stimulus-responsive gel material was obtained.

After the color measurement was completed, the stimulus-responsive gel material was transferred to a container filled with pure water and left to stand for 10 minutes, and it was confirmed that the color of the stimulus-responsive gel material no longer changed and was stabilized.

Thereafter, the stimulus-responsive gel material was taken out from pure water and immersed in an aqueous salt solution for evaluation whose concentration was changed. Then, the stimulus-responsive gel material was left to stand for 5 minutes, and it was confirmed that the color of the stimulus-responsive gel material no longer changed and was stabilized.

Thereafter, with respect to the stimulus-responsive gel material whose color was stabilized, color measurement was performed in the same manner as described above, and the data of the reflection spectrum of the stimulus-responsive gel material was obtained.

By repeating the procedure as described above, within a range in which the concentration of NaCl is 0 mass % or more and 5.0 mass % or less, a graph showing the relationship between the concentration of salt (X axis) and the peak wavelength of a reflected light from the stimulus-responsive gel material (Y axis) was created, and the width of the range of the concentration region in which the absolute value ($|\Delta Y/\Delta X|$) of the slope of the graph is 30 (nm/mass %) or more (hereinafter referred to as "the width of the region in which the sensitivity is a predetermined value or more") was obtained and evaluated according to the following criteria.

A: The width of the region in which the sensitivity is a predetermined value or more is 3.0 mass % or more.

B: The width of the region in which the sensitivity is a predetermined value or more is 2.5 mass % or more and less than 3.0 mass %.

C: The width of the region in which the sensitivity is a predetermined value or more is 2.0 mass % or more and less than 2.5 mass %.

D: The width of the region in which the sensitivity is a predetermined value or more is 1.5 mass % or more and less than 2.0 mass %.

E: The width of the region in which the sensitivity is a predetermined value or more is less than 1.5 mass %.

In the above description, the procedures in which the temperature was not particularly specified were performed at room temperature (25° C.), and also as pure water and the aqueous salt solutions for evaluation, those at 25° C. were used.

These results are summarized in Table 2.

TABLE 2

| | Evaluation |
|---|---|
| Example 1 | A |
| Example 2 | A |
| Example 3 | A |
| Example 4 | A |
| Example 5 | A |
| Example 6 | A |
| Example 7 | B |
| Example 8 | B |
| Example 9 | B |
| Example 10 | B |
| Example 11 | B |
| Comparative Example 1 | C |
| Comparative Example 2 | D |
| Comparative Example 3 | D |
| Comparative Example 4 | D |

As apparent from Table 2, in the case of using the stimulus-responsive gel materials of Examples, the detection of the concentration of salt could be easily and stably performed in a wide concentration range. Further, each of the stimulus-responsive gel materials of Examples had sufficiently high sensitivity even in a range in which the concentration of NaCl was low (a range in which the concentration of NaCl was 0 mass % or more and 1.0 mass % or less). On the other hand, in the case of Comparative Examples, a satisfactory result was not obtained. More specifically, in the case of Comparative Examples, the concentration range in which the detection of the concentration of salt can be stably performed was narrow. Further, in the case of Comparative Examples, the sensitivity was particularly poor in a range in which the concentration of NaCl was low (a range in which the concentration of NaCl was 0 mass % or more and 1.0 mass % or less).

The entire disclosure of Japanese Patent Application No. 2014-025180, filed Feb. 13, 2014 is expressly incorporated by reference herein.

What is claimed is:

1. A stimulus-responsive gel material, comprising:
   a polymeric material containing as constituent components, a first monomer and a second monomer having higher hydrophobicity than the first monomer;
   fine particles having an average particle diameter of 10 nm or more and 1000 nm or less; and
   a solvent,
   wherein the wavelength of a reflected light from the material changes according to the concentration of salt to come in contact with the material, and
   the first monomer is either diacetoneacrylamide or N,N-diethylacrylamide.

2. The stimulus-responsive gel material according to claim 1, wherein the polymeric material has a logP value of 0.62 or more and 0.81 or less.

3. The stimulus-responsive gel material according to claim 1, wherein the first monomer has a logP value of 0.46 or more and 0.78 or less.

4. The stimulus-responsive gel material according to claim 1, wherein the second monomer has a logP value of 1.1 or more and 1.6 or less.

5. The stimulus-responsive gel material according to claim 1, wherein the second monomer has a phenylboronic acid structure.

6. The stimulus-responsive gel material according to claim 1, wherein when the content of the first monomer in the polymeric material is denoted by $X_1$(mol %) and the content of the second monomer therein is denoted by $X_2$ (mol %), $X_1$ and $X_2$ satisfy the following relationship: $0.07 \leq X_2/X_1 \leq 0.45$.

7. The stimulus-responsive gel material according to claim 1, wherein water is contained as the solvent.

* * * * *